(12) United States Patent
Sudo et al.

(10) Patent No.: US 7,734,160 B2
(45) Date of Patent: Jun. 8, 2010

(54) ENDOSCOPE APPARATUS (75) Inventors: Masaru Sudo, Tokyo (JP); Hiroyuki Kuroda, Tokyo (JP); Katsuyuki Saito, Sagamihara (JP)

(73) Assignee: Olympus Corporation (JP)

( * ) Notice: Subject to any disclaimer, the term of this patent is extended or adjusted under 35 U.S.C. 154(b) by 608 days.

(21) Appl. No.: 11/570,873

(22) Filed: Dec. 18, 2006

(65) Prior Publication Data

US 2008/0062261 A1    Mar. 13, 2008

Related U.S. Application Data (63) Continuation of application No. PCT/JP2005/010382, filed on Jun. 7, 2005.

(30) Foreign Application Priority Data

Jun. 17, 2004    (JP)    ............... 2004-179693

(51) Int. Cl.
*A61B 1/04* (2006.01)
*H04N 13/00* (2006.01)
(52) U.S. Cl. .......................... 396/17; 348/45
(58) Field of Classification Search ............. 396/17; 348/45, 65, 76
See application file for complete search history.

(56) References Cited

U.S. PATENT DOCUMENTS

| | | | | |
|---|---|---|---|---|
| 5,817,014 A * | 10/1998 | Hori et al. | .................... | 600/118 |
| 7,123,288 B2 * | 10/2006 | Abe et al. | ..................... | 348/65 |
| 7,365,768 B1 * | 4/2008 | Ono et al. | ..................... | 348/76 |
| 2001/0016680 A1 | 8/2001 | Minami et al. | | |
| 2003/0063398 A1 | 4/2003 | Abe et al. | | |
| 2003/0076410 A1 * | 4/2003 | Beutter et al. | ................. | 348/65 |

FOREIGN PATENT DOCUMENTS

| | | |
|---|---|---|
| JP | 08-336497 | 12/1996 |
| JP | 09-322566 | 12/1997 |
| JP | 2000-10023 | 1/2000 |
| JP | 2000-010023 | 1/2000 |
| JP | 2000-338420 | 12/2000 |

(Continued)

OTHER PUBLICATIONS

English Translation of Chinese official communication dated Apr. 11, 2008 relating to Application No. 2005800193573.

(Continued)

*Primary Examiner*—Rodney E Fuller
(74) *Attorney, Agent, or Firm*—Ostrolenk Faber LLP (57) ABSTRACT

An endoscope apparatus including: an endoscope unit having: a lens units; a photographing unit for photographing an optical image picked up through the lens unit; and a lens unit driving motor for driving the lens unit for realizing at least one of a zoom function and a focus function; and a control unit having: an image processing circuit for processing an image signal output from the photographing unit, and for outputting the processed image signal to a monitor, wherein: at least one of the endoscope unit and the control unit comprises: a motor driving circuit for controlling the lens unit driving motor; and a motor control circuit for outputting a control signal that controls the motor driving circuit by detecting a switch signal generated by operation of a zoom switch or a focus switch.

4 Claims, 11 Drawing Sheets

FOREIGN PATENT DOCUMENTS

| | | |
|---|---|---|
| JP | 2002-58636 | 2/2002 |
| JP | 2002-058636 | 2/2002 |
| WO | WO 2004/039250 | 5/2004 |

OTHER PUBLICATIONS

Korean Office Action dated Aug. 8, 2008 (with English translation of relevant parts).

Supplementary European Search Report dated Aug. 12, 2009 in corresponding European Patent Application No. EP 05 74 8631 (English language).

European Official Communication dated Nov. 9, 2009.

* cited by examiner

| BIT | DATA |
|---|---|
| D0 | START BIT:0 |
| D1 | CAMERA HEAD ZOOM SW : TELE |
| D2 | CAMERA HEAD ZOOM SW : WIDE |
| D3 | CAMERA HEAD FOCUS SW : NEAR |
| D4 | CAMERA HEAD FOCUS SW : FAR |
| D5 | ZOOM POSITION DETECTION : PIZ(0) |
| ⋮ | ⋮ |
| D12 | ZOOM POSITION DETECTION : PIZ(7) |
| D13 | FOCUS POSITION DETECTION : PIF(0) |
| ⋮ | ⋮ |
| D20 | FOCUS POSITION DETECTION : PIF(7) |

F I G. 1 0 B

SD2 — | D0 | D1 | D2 | D3 | D4 |

F I G. 1 0 C

| BIT | DATA |
|---|---|
| D0 | START BIT : 0 |
| D1 | TELE INSTRUCTION |
| D2 | WIDE INSTRUCTION |
| D3 | NEAR INSTRUCTION |
| D4 | FAR INSTRUCTION |

ENDOSCOPE APPARATUS

CROSS REFERENCE TO RELATED APPLICATIONS

This is a Continuation Application of PCT Application No. PCT/JP 2005/10382, filed Jun. 7, 2005, which was not published under PCT Article 21(2) in English.

This application is based upon and claims the benefit of priority from the prior Japanese Patent Application No. 2004-179693, filed Jun. 17, 2004, the entire contents of which are incorporated herein by reference.

BACKGROUND OF THE INVENTION

1. Field of the Invention

The present invention relates to an endoscope apparatus.

2. Description of the Related Art

The conventional endoscope apparatus has a zoom control unit for controlling the enlargement and reduction in size of an optical image that is provided separately from a CCU (Camera Control Unit), as disclosed, for example, by Japanese Patent Application Publication No. 9-322566 and Japanese Patent Application Publication No. 8-336497.

Summary of the Invention

The endoscope apparatus according to the present invention includes an endoscope unit having a lens unit; a photographing unit for photographing an optical image picked up through the lens unit, and a lens unit driving motor for driving the lens unit for realizing at least one of a zoom function and a focus function, and a control unit having an image processing circuit for processing an image signal output from the photographing unit, and for outputting the processed image signal to a monitor, in which at least one of the endoscope unit and the control unit comprises a motor driving circuit for controlling the lens unit driving motor, and a motor control circuit for outputting a control signal that controls the motor driving circuit by detecting a switch signal generated by operation of a zoom switch or a focus switch.

Also, the endoscope apparatus according to the present invention comprises an endoscope unit having a lens unit, a photographing unit for photographing an optical image picked up through the lens unit, and a lens unit driving motor for driving the lens unit for realizing at least one of a zoom function and a focus function, and a control unit having an image processing circuit for processing an image signal output from the photographing unit, and for outputting the processed image signal to a monitor, a motor driving circuit for controlling the lens unit driving motor, and a motor control circuit for outputting a control signal that controls the motor driving circuit by detecting a switch signal generated by operation of a zoom switch or a focus switch.

Also, the endoscope apparatus according to the present invention comprises an endoscope unit having a lens unit, a photographing unit for photographing an optical image picked up through the lens unit, and a lens unit driving motor for driving the lens unit for realizing at least one of a zoom function and a focus function a motor driving circuit for controlling the lens unit driving motor, and a motor control circuit for outputting a control signal that controls the motor driving circuit by detecting a switch signal generated by operation of a zoom switch or a focus switch and a control unit having an image processing circuit for processing an image signal output from the photographing unit, and for outputting the processed image signal to a monitor.

Further, in the above endoscope apparatus, the control unit further comprises an operation unit, and a control circuit for providing, to the motor control circuit, a control signal for controlling the motor driving circuit on the basis of a switch signal generated by operation of the operation unit and a switch signal generated by operation of the zoom switch or the focus switch.

Also, in the above endoscope apparatus, the endoscope unit further comprises a determination information notification unit for notifying determination information used for the determination of whether the endoscope unit has a zoom function and a focus function, and the control unit further comprises a control unit for controlling operation of the motor driving circuit and the motor control circuit on the basis of the determination information notified by the determination information notification unit.

DESCRIPTION OF THE PREFERRED EMBODIMENTS

In the above conventional technique, the zoom control unit is provided separately from the CCU, and this has prevented the size of endoscope apparatuses from being reduced.

An endoscope apparatus according to the present invention realizes size reduction by integrating a drive/control system used for zoom control and focus control into an existing circuit.

Hereinafter, embodiments of the present invention will be explained in detail by referring to the drawings.

Figure 1:
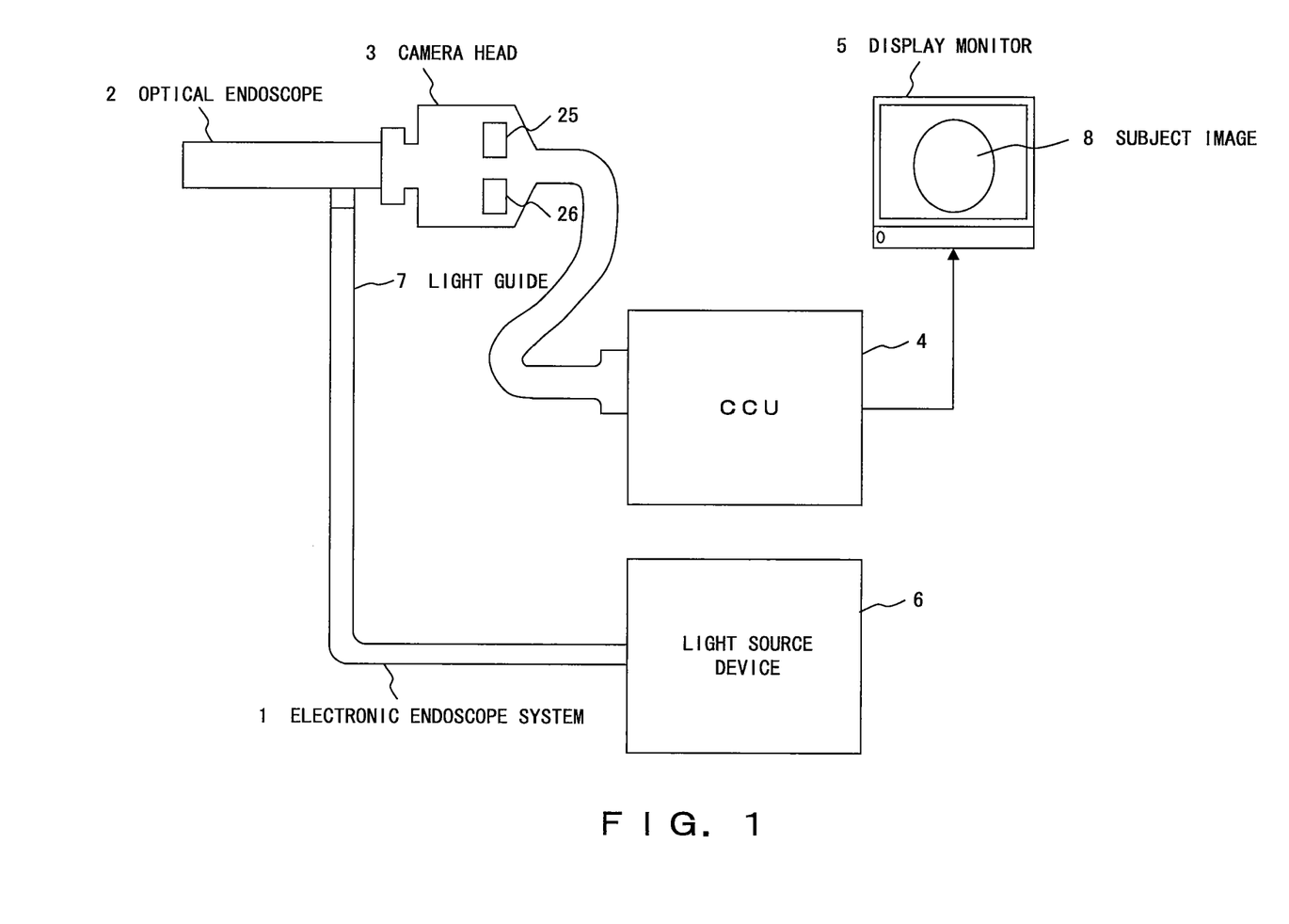
FIG. 1 shows a configuration of an endoscope system to which the present invention can be applied.

FIG. 1 shows a configuration of an endoscope system to which the present invention can be applied. As an endoscope unit including a photographing device such as a CCD or the like, an optical endoscope 2 inserted into a coelum of a patient is connected to a camera head 3. As a control unit including a CPU and an image signal processing circuit, the camera head 3 is connected to a CCU (Camera Control Unit) 4. The camera head 3 is provided with a zoom switch (hereinafter, referred to as "zoomSW") 25 and a focus switch (hereinafter, referred to as "focus SW") 26. The CCU 4 is connected to a display monitor 5. A light source device 6 is connected through a light guide 7 to the optical endoscope 2. Note that a video scope in which the optical endoscope 2, the camera head 3, and the light guide 7 are integrated may be employed as a configuration of the present invention.

Note also that a videoscope in which a camera head and a light guide are integrated together with a rigid endoscope, a flexible endoscope, or an optical endoscope may be employed as the optical endoscope 2.

First Embodiment

Figure 2:
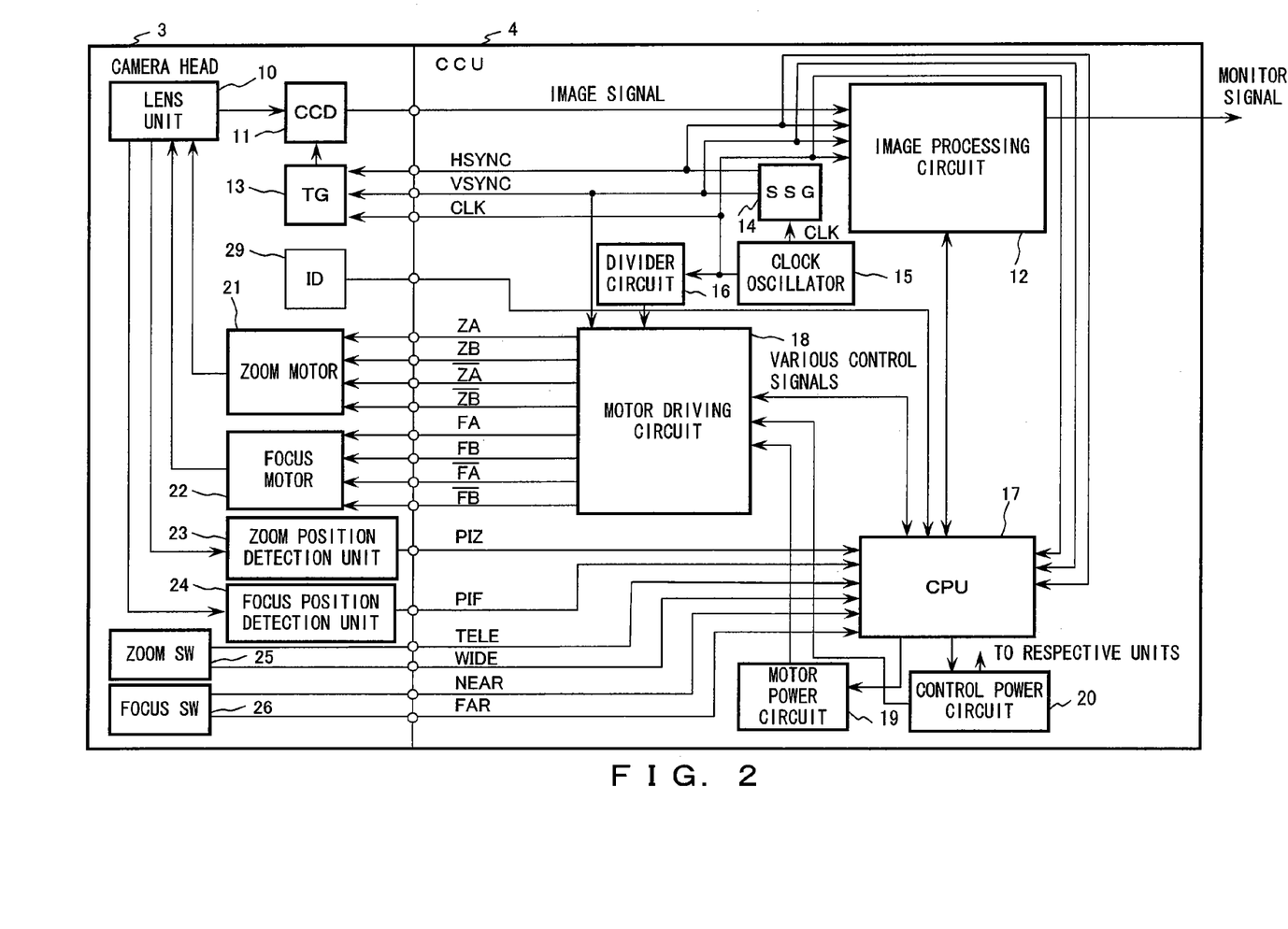
FIG. 2 is a block diagram that shows a configuration of the endoscope apparatus according to the first embodiment of the present invention with a connected camera head that has a zoom function and a focus function.

FIG. 2 is a block diagram that shows a configuration of an endoscope apparatus according to the first embodiment of the present invention when a camera head having a zoom function and a focus function is connected. The camera head 3 includes a lens unit 10, a CCD (photographing device) 11, a TG (Timing Generator) 13, a zoom motor 21, a focus motor 22, a zoom position detection unit 23, a focus position detection unit 24, the zoom SW 25, the focus SW 26, and an ID storage unit 29.

The lens unit 10 includes a zoom lens and a focus lens. Information used for discriminating types of camera heads (e.g., whether or not the camera unit has zoom and focus functions) is stored in the ID storage unit 29.

The CCU 4 includes an image processing circuit 12, an SSG (Synchronization Signal Generator) 14, a clock oscillator 15, a divider circuit 16, a motor driving circuit 18, a CPU 17, a motor power circuit 19, and a control power circuit 20.

When the endoscope apparatus begins operation, the camera head 3 is connected to the CCU 4 first. Then, the ID storage unit 29 in the camera head 3 sends an ID signal of the camera head 29 to the CPU 17 of the CCU 4.

The CPU 17 determines whether the camera head 3 that is currently connected to the CCU 4 is a camera head for zooming/focusing on the basis of the ID signal. When it is determined that the camera head 3 that is currently connected to the CCU 4 is a camera head for zooming/focusing (i.e., the case shown in FIG. 2), the processes below are executed.

An observation image of observation target tissue is picked up by an optical endoscope 1 inserted into the body of a patient and is photographed by the CCD 11. An image signal from the CCD 11 is input into the image processing circuit 12 and is subjected to a prescribed image process. The signal that has been subjected to the image process is sent to the display monitor 5 (FIG. 1) as a display signal and is displayed as a subject image 8.

The clock oscillator 15 generates a clock signal CLK having a prescribed frequency. This clock signal CLK is sent to the SSG 14 where a horizontal synchronization signal (HSYNC), a vertical synchronization signal (VSYNC), and synchronization signals of other types are generated. The HSYNC and the VSYNC are sent to the timing generator (TG) 13 together with the CLK, the image processing circuit 12, and the CPU 17. The TG 13 generates a signal that determines the timing at which the CCD 11 photographs the image.

Figure 3:
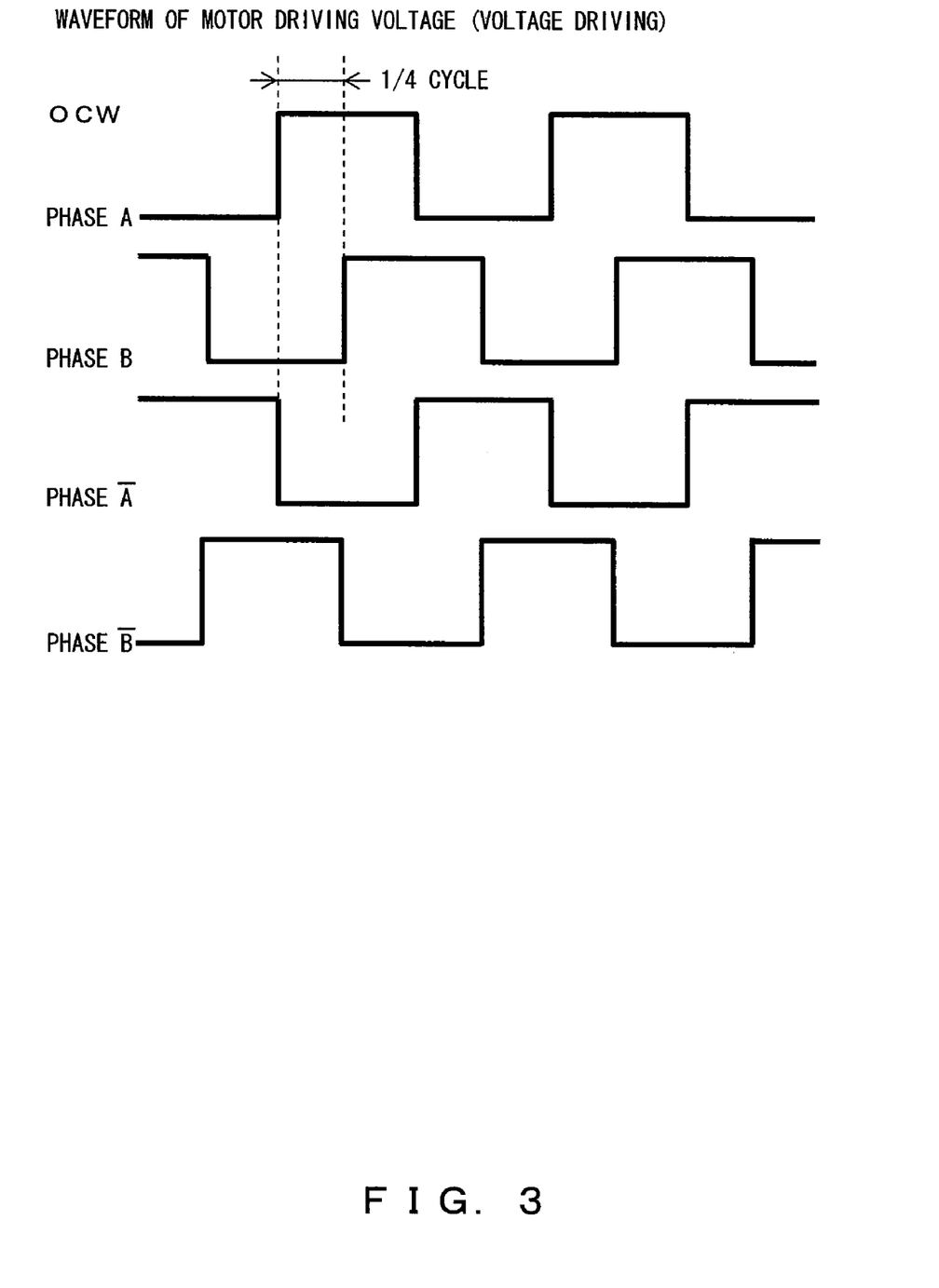
FIG. 3 shows the waveform of a motor driving voltage (voltage driving)

When a user operates the zoom SW 25, a TELE or WIDE switch signal is sent to the CPU 17. The CPU 17 sends a control signal that causes the zoom lens to operate in accordance with the signal to the motor driving circuit 18. The motor driving circuit 18 operates in accordance with the signal obtained by dividing the CLK from the clock oscillator 15 by using the divider circuit 16. The motor driving circuit 18 generates signals ZA, ZB, ZA (inverted), and ZB (inverted) that drive the zoom motor 21 in accordance with the control signal from the CPU 17. Herein, ZA is a signal represented by phase A of a waveform of a zoom motor driving voltage, ZB is a signal represented by phase B (shifted from phase A by ¼ cycle) of the waveform of the zoom motor driving voltage, ZA (inverted) is a signal obtained by inverting ZA, and ZB (inverted) is a signal obtained by inverting ZB. An example of phase A, phase B, phase A (inverted), and phase B (inverted) is shown in FIG. 3.

The zoom motor 21 moves the zoom lens in the lens unit 10 in the TELE direction or in the WIDE direction on the basis of these signals. When the position of the zoom lens is detected by the zoom position detection unit 23 comprising a photo interrupter or the like, the position information is provided to the CPU 17 as a PIZ signal by the zoom position detection unit 23. Thereby, the CPU 17 can move the zoom lens to desired positions.

When the user operates the focus SW 26, a switch signal of NEAR or FAR is sent to the CPU 17. The CPU 17 sends a control signal that causes the zoom lens to operate in accordance with the signal to the motor driving circuit 18. The motor driving circuit 18 generates signals FA, FB, FA (inverted), and FB (inverted) to drive the focus motor 22 in accordance with the control signal from the CPU 17. FA is a signal represented by phase A of a waveform of a focus motor driving voltage, FB is a signal represented by phase B (shifted from phase A by ¼ cycle) of the waveform of the focus motor driving voltage, FA (inverted) is a signal obtained by inverting FA, and FB (inverted) is a signal obtained by inverting FB. An example of phase A, phase B, phase A (inverted), and phase B (inverted) is shown in FIG. 3.

The focus motor 22 moves the focus lens in the lens unit 10 to both proximal and distal positions in accordance with the signals. When the position of the focus lens is detected by the focus position detection unit 24 that includes a photo interrupter or the like, the position information is provided to the CPU 17 as a PIF signal by the focus position detection unit 24. Thereby, the CPU 17 can move the focus lens to a focus position.

When the camera head having zoom/focus functions is detected as above, the CPU 17 controls the control power circuit 20, the motor power circuit 19, and the motor driving circuit 18 in order to control the zoom/focus operations.

Figure 4:
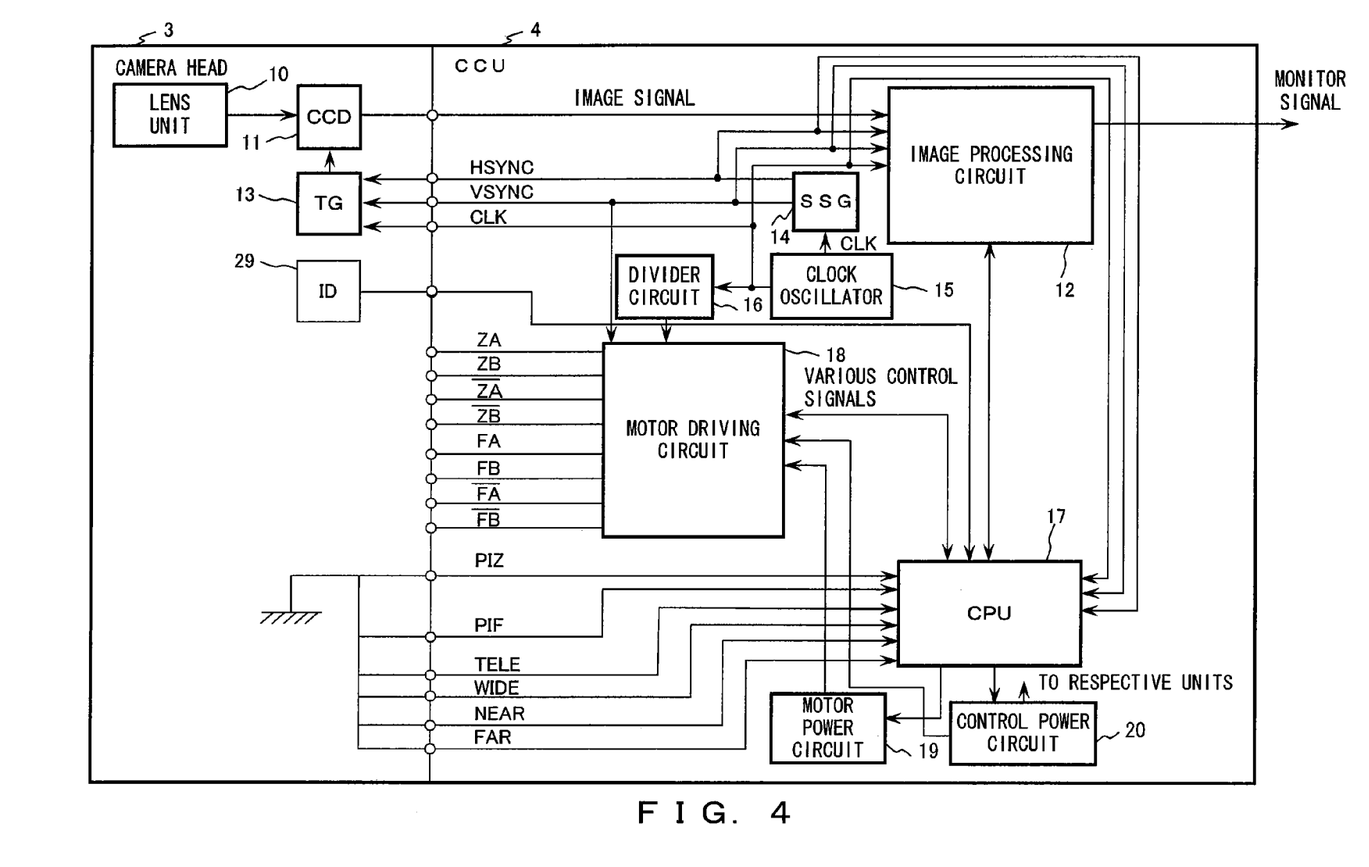
FIG. 4 is a block diagram that shows a configuration of the endoscope apparatus according to the first embodiment of the present invention with a connected camera head that does not have a zoom function or a focus functions.

FIG. 4 is a block diagram that shows a configuration of an endoscope apparatus according to the first embodiment of the present invention with a camera head connected that does not have a zoom function or focus functions. FIG. 2 explains the case in which the camera head has a zoom function and a focus function connected. In FIG. 4, the case is explained in which a camera head that does not have a zoom function or a focus function is connected.

When the endoscope apparatus operates, the camera head 3 is first connected to the CCU 4. Then, the ID storage unit 29 in the camera head 3 sends an ID signal for the camera head 29 to the CPU 17 of the CCU 4.

The CPU 17 determines whether or not the camera head 3 that is currently connected to the CCU 4 is a camera head for zooming/focusing on the basis of the ID signal. When it is determined that the camera head 3 that is currently connected to the CCU 4 is not a camera head for zooming/focusing (i.e., the case in FIG. 4), the CPU 17 does not send a control signal to the motor driving circuit 18. Also, the CPU 17 sends the control signal to the motor power circuit 19 and control power circuit 20 in order to shut down the power of the motor power circuit 19 and control power circuit 20. Thereby, wastes of power can be reduced.

Signal lines of input signals (PIZ, PIF, TELE, WIDE, NEAR, and FAR) from the camera head 3 to the CCU 4 are fixed at a Low level (GND fix). In addition, there is no signal line of output signals (ZA, ZB, ZA (inverted), ZB (inverted), FA, FB, FA (inverted), and FB (inverted)) from the CCU 4 to the camera head 3 on the camera head side, and they are opened.

According to the first embodiment of the present invention, the drive/control system for the zoom control and the focus control is integrated into the CCU 4 so that the size of the entire electronic endoscope apparatus can be reduced. Also, because the drive/control system for the zoom control and the focus control is integrated into the CCU 4, the number of components operated by a user can be reduced so that the use of the electronic endoscope apparatus becomes more user-friendly. Further, there can be a reduction in the unnecessary consumption (waste) of electric power of the motor power circuit 19 and the control power circuit 20.

Second Embodiment

Figure 5:
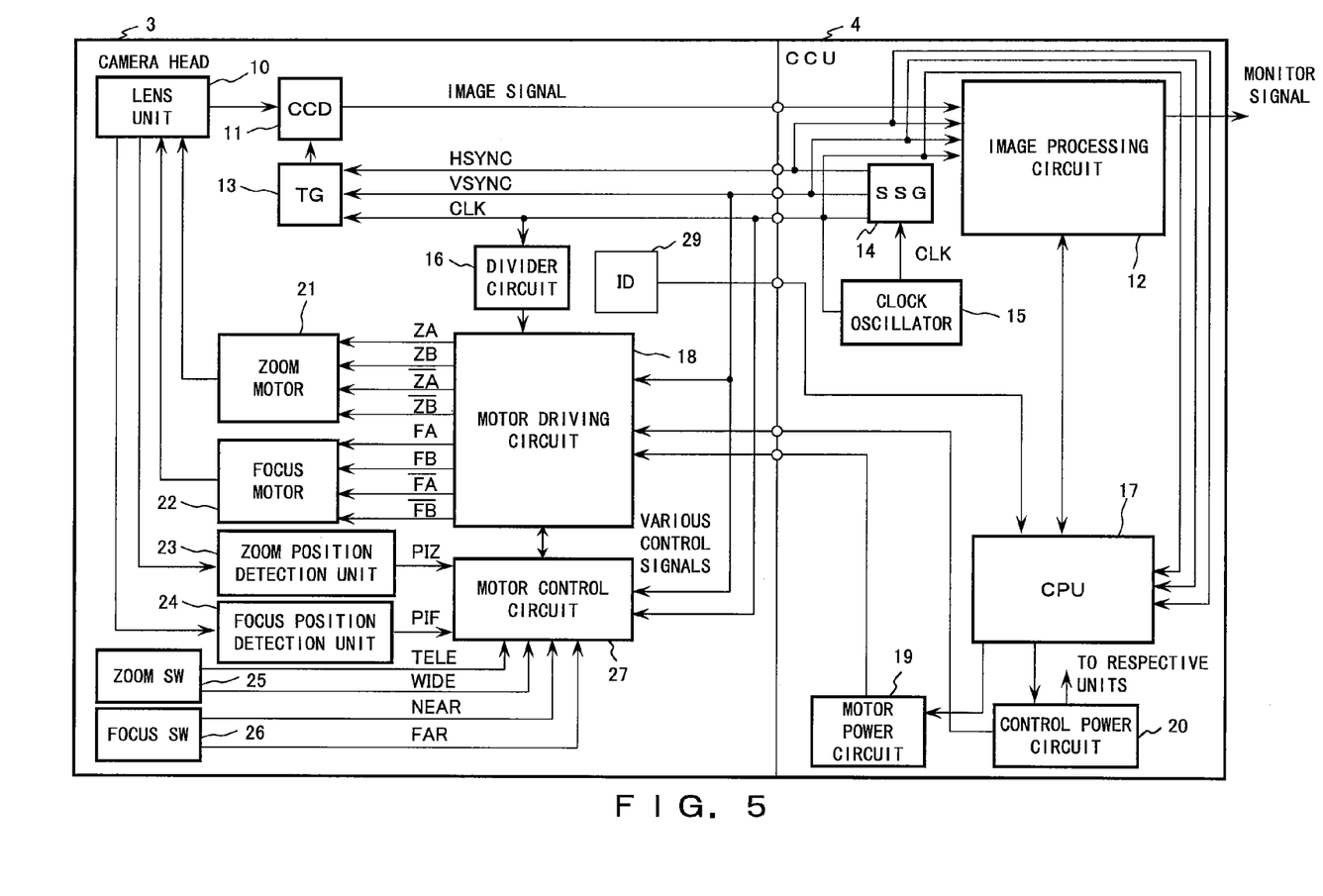
FIG. 5 is a block diagram that shows a configuration of the endoscope apparatus according to the second embodiment of the present invention with a connected camera head that has a zoom function and a focus function.

FIG. 5 is a block diagram that shows a configuration of the endoscope apparatus according to the second embodiment of the present invention with a camera head connected that has a zoom function and a focus function is. In this embodiment, the case is explained in which the motor driving circuit 18, a motor control circuit 27, and the divider circuit 16 explained in FIG. 2 are included in the camera head 3.

When the endoscope apparatus operates, the camera head 3 is first connected to the CCU 4. Then, as with the first embodiment, it is determined that the camera head that is currently connected has a zoom function and a focus function.

Figure 6:
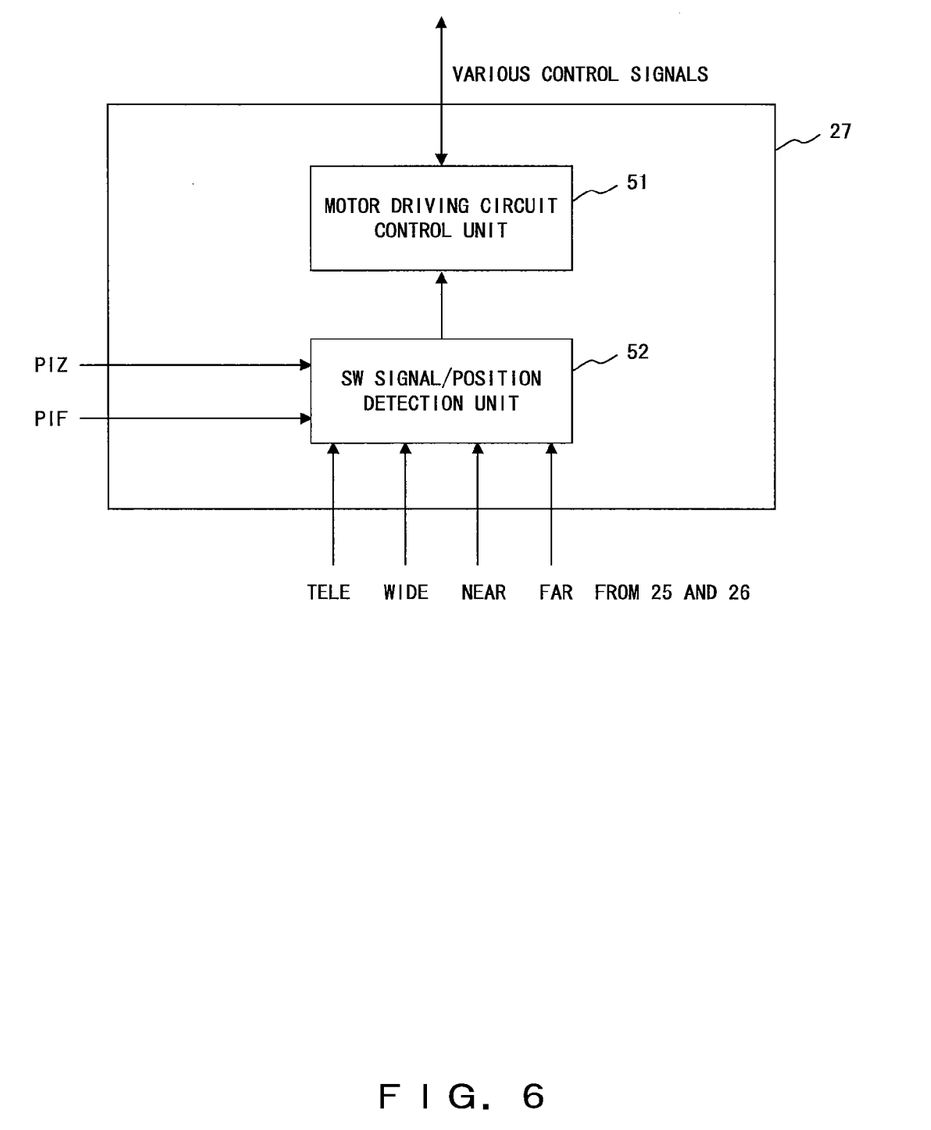
FIG. 6 shows the configuration of the motor control circuit 27 according to the second embodiment of the present invention.

FIG. 6 shows a configuration of the motor control circuit 27 according to the second embodiment in which a motor driving circuit control unit 51 and an SW signal/position detection unit 52 are included. The SW signal/position detection unit 52 detects a switch signal generated by operation of the zoom SW 25 or the focus SW 26. Also, the SW signal/position detection unit 52 receives the PIZ signal from the zoom position detection unit 23 and the PIF signal from the focus position detection unit 24, and sends an instruction signal to the motor driving circuit control unit 51. Receiving the instruction signal from the SW signal/position detection unit 52, the motor driving circuit control unit 51 sends various control signals to the motor driving circuit 18.

Figure 7:
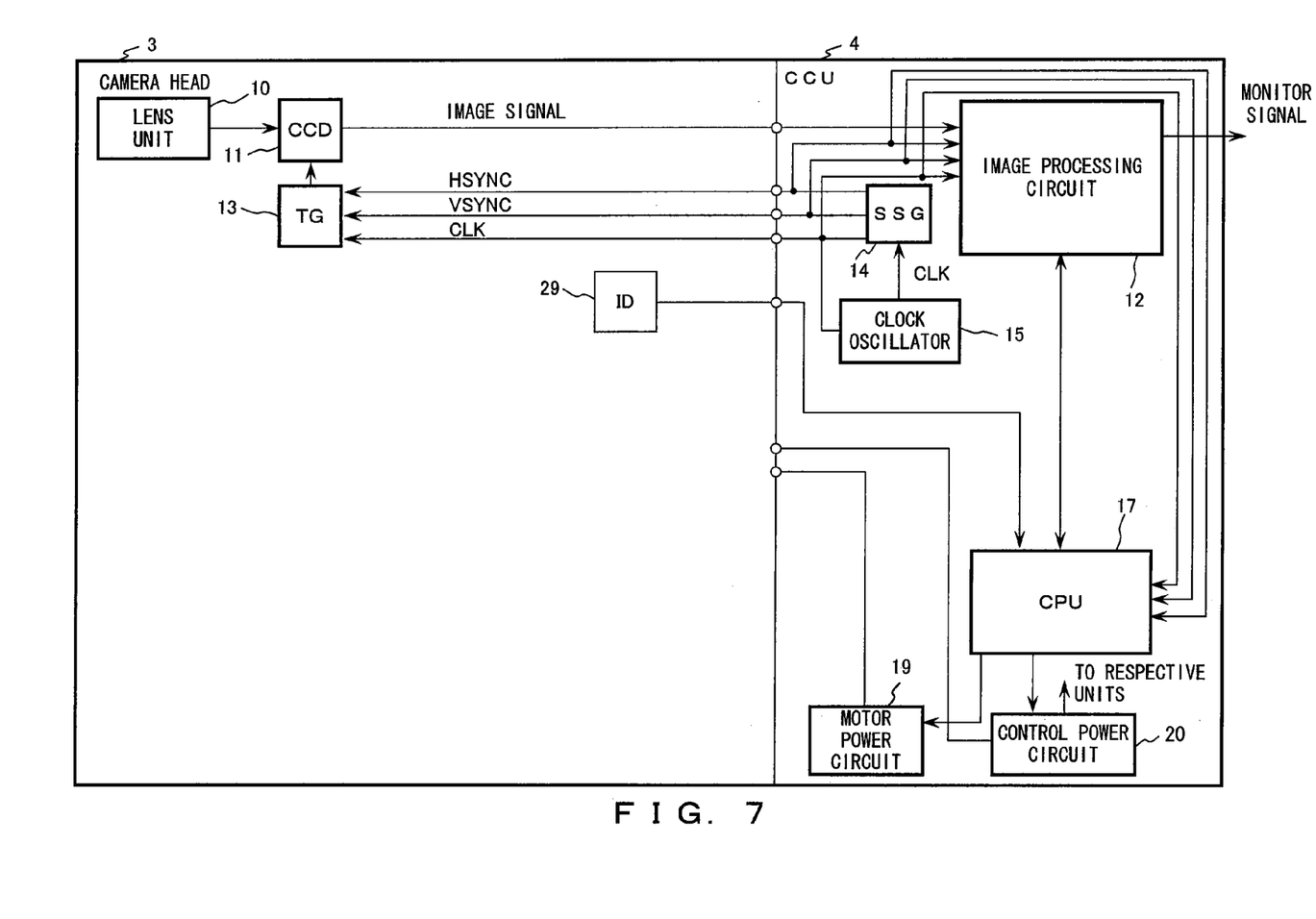
FIG. 7 is a block diagram that shows a configuration of the endoscope apparatus according to the second embodiment of the present invention with a connected camera head that does not have a zoom function or a focus function.

FIG. 7 is a block diagram that shows a configuration of the endoscope apparatus according to the second embodiment of the present invention with a camera head connected that does not have a zoom function or a focus function. When the endoscope apparatus operates, the camera head 3 is connected to the CCU 4. Then, as with the first embodiment, it is determined that the camera head that is currently connected is a camera head that does not have a zoom function or a focus function. Then, the CPU 17 sends the control signal to the motor power circuit 19 and the control power circuit 20 in order to shut down the power of the motor power circuit 19 and the control power circuit 20. Thereby, there can be a reduction in the unnecessary consumption (waste) of power.

According to the second embodiment, the drive/control system for the zoom control and the focus control is included in the camera head 3 so that the size of the apparatus can be reduced and the total number of connector pins (the number of signal lines) between the camera head 3 and the CCU 4 can be greatly reduced. The number of signal lines between the camera head 3 and the CCU 4 is actually two: one for the motor power circuit 19 and the other for the control power circuit 20. Also, the unnecessary consumption (waste) of power of the motor power circuit 19 and the control power circuit 20 can be reduced.

Third Embodiment

Figure 8:
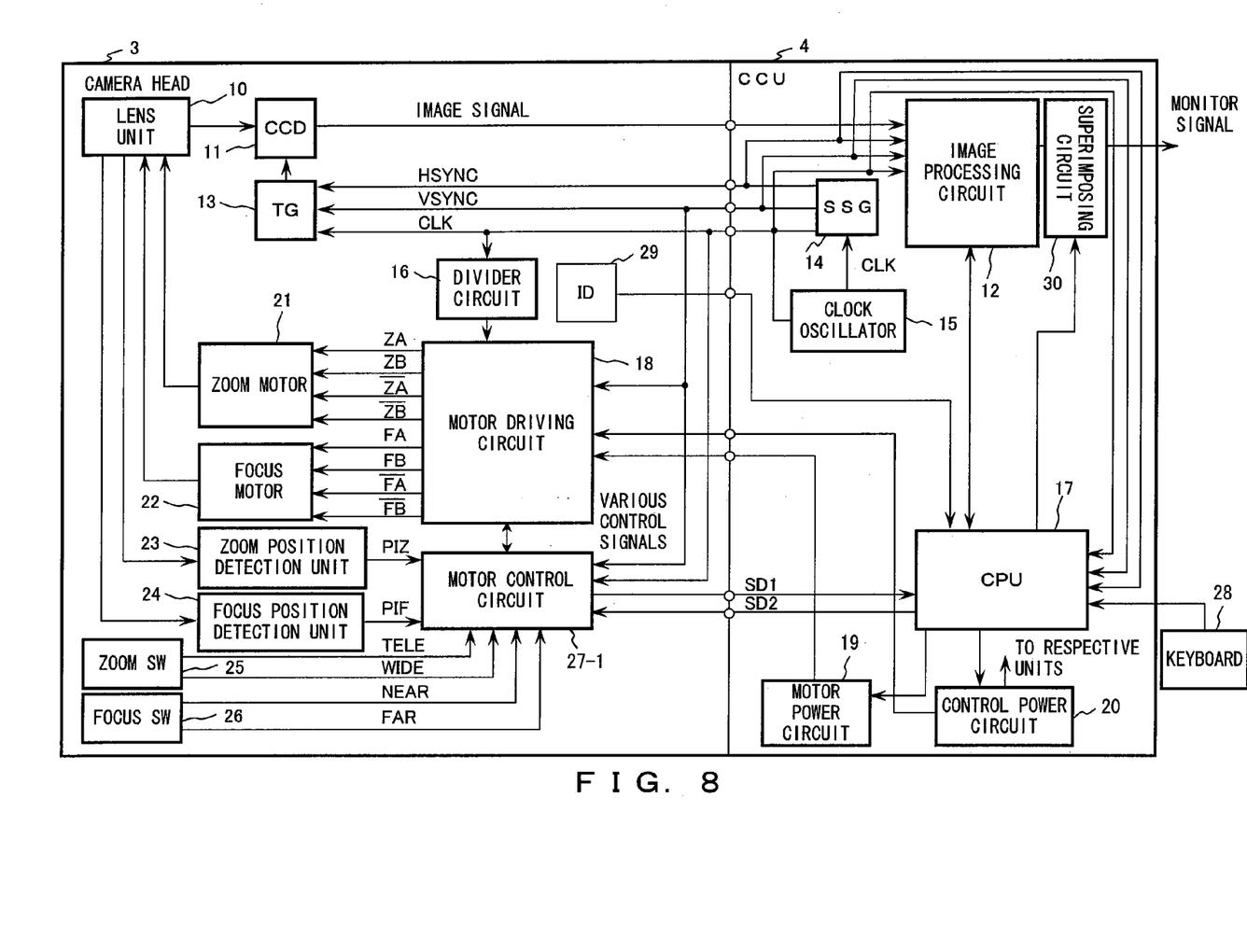
FIG. 8 is a block diagram that shows a configuration of the endoscope apparatus according to a third embodiment of the present invention with a camera head connected that has a zoom function and a focus function.

FIG. 8 is a block diagram that shows a configuration of the endoscope apparatus according to the third embodiment of the present invention with a camera head connected that has a zoom function and a focus function. When the endoscope apparatus operates, the camera head 3 is first connected to the CCU 4. Then, as with the first embodiment, the CPU 17 determines that the camera head 3 that is currently connected has a zoom function and a focus function on the basis of the information read from the ID information storage unit.

In this embodiment, as in the second embodiment, the motor driving circuit 18, the motor control circuit 27, and the divider circuit 16 are included in the camera head 3. Also, wiring is provided such that bidirectional serial communications can be conducted between a motor control circuit 27-1 in the camera head 3 and the CPU 17 of the CCU 4. Further, a keyboard 28 whose keys can act as switches for giving instructions for zoom and focus operations is connected to the cup 17.

Figure 9:
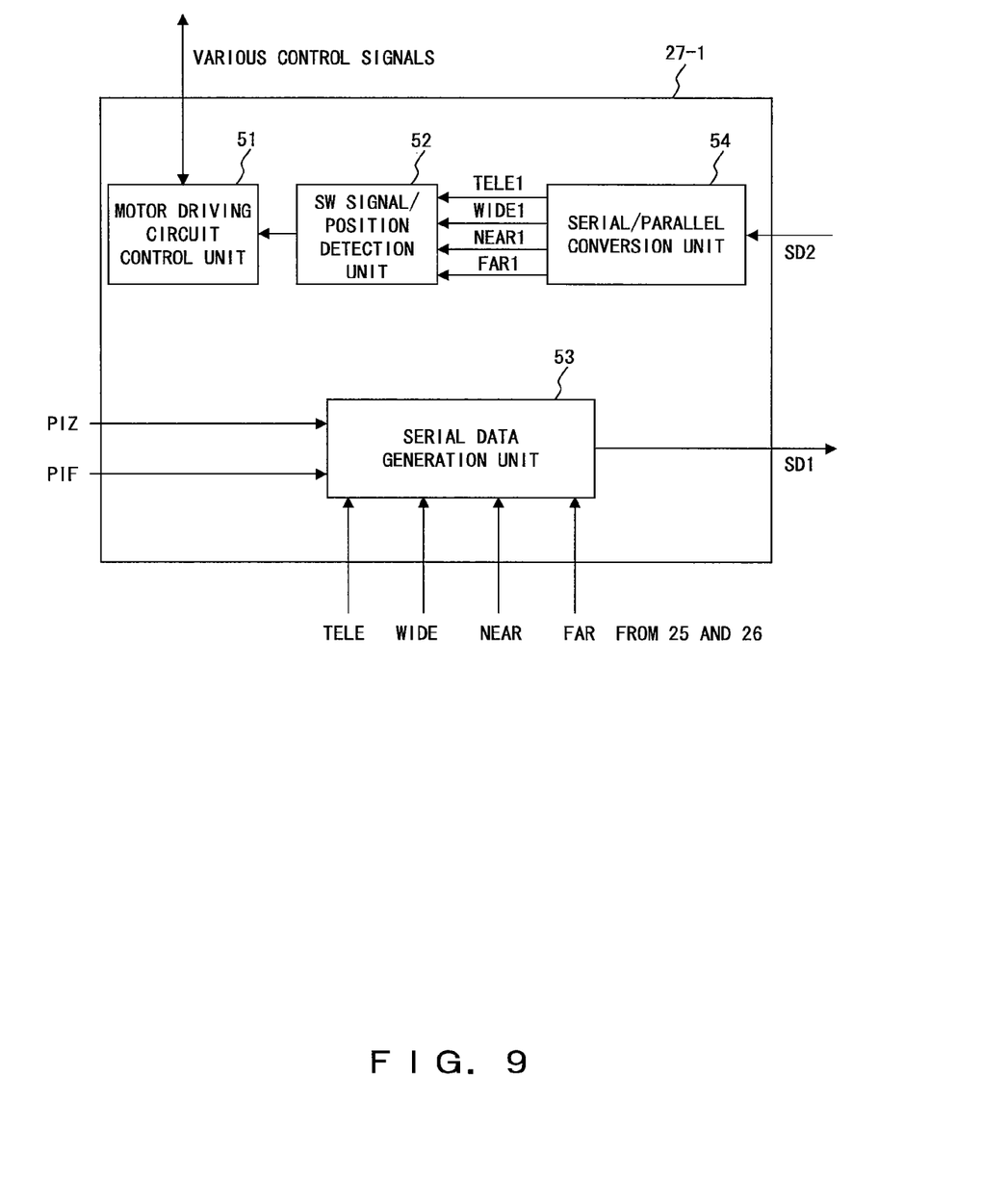
FIG. 9 shows a configuration of a motor control circuit 27-1 according to the third embodiment of the present invention.

FIG. 9 shows a configuration of the motor control circuit 27-1 in the third embodiment comprising the motor driving circuit control unit 51, the SW signal/position detection unit 52, a serial/parallel conversion unit 54, and a serial data generation unit 53.

In the third embodiment, the CPU 17 receives not only the switch signal generated by operation of the zoom SW 25 or the focus SW 26, but also a switch signal generated by operation of the keyboard 28, such that the zoom operation and the focus operation can be controlled through the keyboard 28.

Figure 10A:
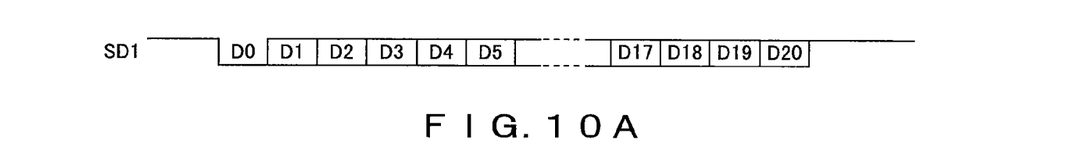
FIGS. 10A through 10D show bit sequences and bit contents of serial data SD1 and SD2.
Figure 10B:
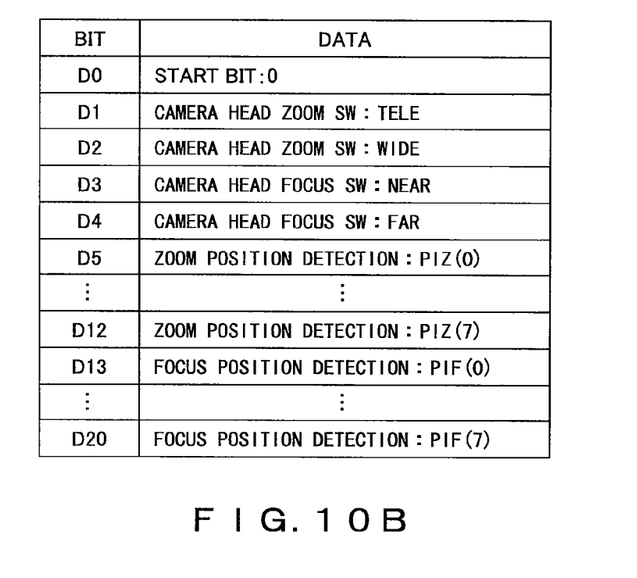

Specifically, the switch signals (TELE and WIDE) generated by operation of the zoom SW 25 of the camera head 25, the switch signals (NEAR and FAR) generated by operation of the focus SW 26, the PIZ signal from the zoom position detection unit 23, and the PIF signal from the focus position detection unit 24 are input into the serial data generation unit 53 and also into the CPU 17 as serial data SD1. FIG. 10A shows a bit sequence of the serial data SD1. FIG. 10B shows the contents of the bits.

Figure 10C:
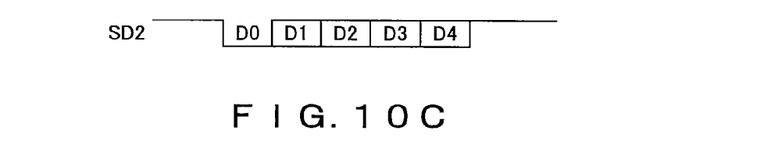
Figure 10D:
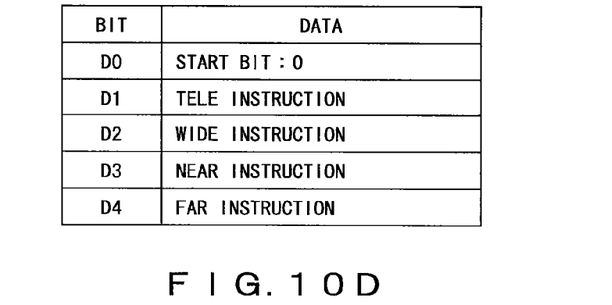

The CPU 17 of the CCU 4 generates a signal as serial data SD2 for controlling the motor driving circuit 18 on the basis of the data SD1 and the switch signal generated by operation of the keyboard 28. FIG. 10C shows a bit sequence of the serial data SD2. FIG. 10D shows the contents of the bits.

The serial/parallel conversion unit 54 receives the serial data SD2 from the CPU 17 and converts it into parallel signals of TELE1, WIDE1, NEAR1, and FAR1. The SW signal/position detection unit 52 detects these parallel signals and sends an instruction signal to the motor driving circuit control unit 51. Receiving the instruction signal from the SW signal/position detection unit 52, the motor driving circuit control unit 51 sends various control signals to the motor driving circuit 18.

A superimposing circuit 30 is used for superimposing current zoom magnification information and a current focus position onto an endoscopy image. The superimposing circuit 30 includes a selector by which an image signal output from the image processing circuit 12 and a signal including the zoom magnification information and the current position output from the CPU 17 are switched to be output as a monitor signal.

Figure 11:
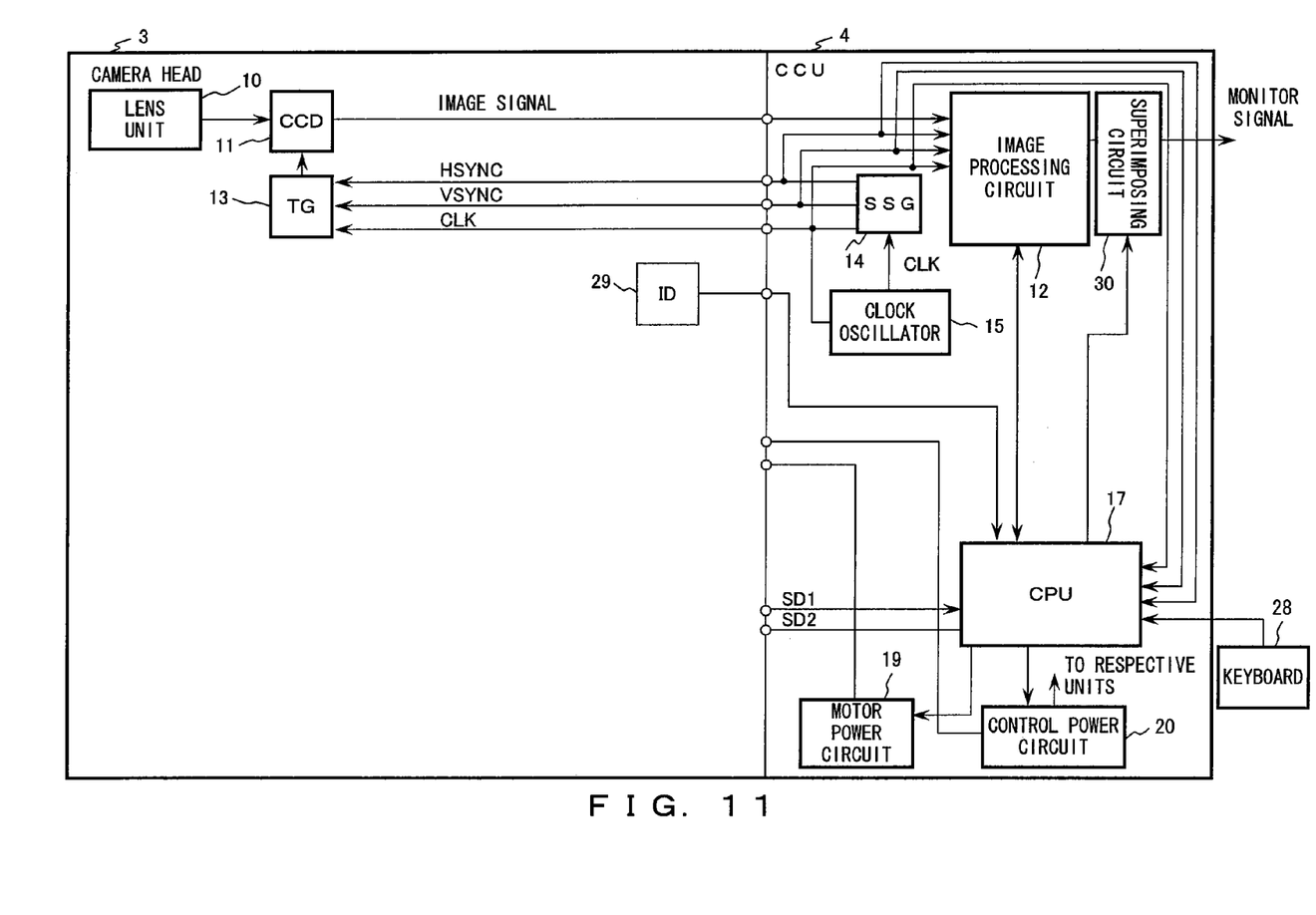
FIG. 11 is a block diagram that shows a configuration of the endoscope apparatus according to the third embodiment of the present invention with a connected camera head that does not have a zoom function or a focus function.

FIG. 11 is a block diagram for showing a configuration of the endoscope apparatus according to the third embodiment of the present invention with a camera head connected that does not have a zoom function or a focus function. When the endoscope apparatus operates, the camera head 3 is first connected to the CCU 4. Then, as with the first embodiment, the CPU 17 determines that the camera head 3 that is currently connected is a camera head that does not have a zoom function or a focus function on the basis of the information read from the ID information storage unit. Next, the CPU 17 sends the control signal to the motor power circuit 19 and the control power circuit 20 in order to shut down the power of the motor power circuit 19 and control power circuit 20. Thereby, the unnecessary consumption (waste) of power can be reduced.

According to the third embodiment, in addition to the effects of the second embodiment, it is possible to control the zoom operation and the focus operation through peripheral devices such as the keyboard 28 and the like. Further, the superimposing circuit 30 that is in sequence after the image processing circuit 12 can superimpose, onto the image signal from the image processing circuit 12, the current zoom magnification information and the current focus position obtained from the PIZ signal and the PIF signal sent to the CPU 17. The superimposing circuit 30 does this in order to display the image with its current zoom magnification information and the current focus position on the display monitor 5.

Additionally, the ID information is used to determine the type of connected camera head in the first through third embodiments. Note however that the scope of the present invention is not limited to these embodiments, and the type of camera head may, for example, be determined by detecting the value of resistance that is set for each type of camera head.

As described above, according to the present invention, the drive/control system for the control of the zoom operation and the focus operation is integrated into an existing circuit; accordingly, the size of the endoscope apparatus can be reduced.

What is claimed is:

1. An endoscope apparatus including:
   an endoscope unit having:
   a lens unit;
   a photographing unit for photographing an optical image picked up through the lens unit; and
   a lens unit driving motor for driving the lens unit for realizing at least one of a zoom function and a focus function; and
   a control unit having:
   an image processing circuit for processing an image signal output from the photographing unit, and for outputting the processed image signal to a monitor, wherein;
   at least one of the endoscope unit and the control unit comprises:
   a motor driving circuit for controlling the lens unit driving motor; and
   a motor control circuit for outputting a control signal that controls the motor driving circuit by detecting a switch signal generated by operation of a zoom switch or a focus switch
   the endoscope unit farther comprises:
   a determination information notification unit for notifying determination information used for the determination of whether or not the endoscope unit has a zoom function and a focus function; and
   the control unit farther comprises:
   a control unit for controlling the operation of the motor driving circuit and the motor control circuit on the basis of the determination information notified by the determination information notification unit.

2. An endoscope apparatus, comprising:
   an endoscope unit having:
   a lens unit;
   a photographing unit for photographing an optical image picked up through the lens unit; and
   a lens unit driving motor for driving the lens unit for realizing at least one of a zoom function and a focus function; and
   a control unit having:
   an image processing circuit for processing an image signal output from the photographing unit and for outputting the processed image signal to a monitor;
   a motor driving circuit for controlling the lens unit driving motor; and
   a motor control circuit for outputting a control signal that controls the motor driving circuit by detecting a switch signal generated by operation of a zoom switch or a focus switch,
   the endoscope unit further comprises:
   a determination information notification unit for notifying determination information used for the determination of whether or not the endoscope unit has a zoom function and a focus function; and
   the control unit further comprises:
   a control unit for controlling the operation of the motor driving circuit and the motor control circuit on the basis of the determination information notified by the determination information notification unit.

3. An endoscope apparatus, comprising:
   an endoscope unit having:
   a lens unit;
   a photographing unit for photographing an optical image picked up through the lens unit;
   a lens unit driving motor for driving the lens unit for realizing at least one of a zoom function and a focus function;
   a motor driving circuit for controlling the lens unit driving motor; and
   a motor control circuit for outputting a control signal that controls the motor driving circuit by detecting a switch signal generated by operation of a zoom switch or a focus switch; and
   a control unit having:
   an image processing circuit for processing an image signal output from the photographing unit and for outputting the processed image signal to a monitor,
   the endoscope unit further comprises:
   a determination information notification unit for notifying determination information used for the determination of whether or not the endoscope unit has a zoom function and a focus function; and
   the control unit further comprises:
   a control unit for controlling the operation of the motor driving circuit and the motor control circuit on the basis of the determination information notified by the determination information notification unit.

4. The endoscope apparatus according to claim 3, wherein:
the control unit further comprises:
- an operation unit; and
- a control circuit for providing, to the motor control circuit, a control signal for controlling the motor driving circuit on the basis of a switch signal generated by operation of the operation unit and a switch signal generated by operation of the zoom switch or the focus switch.

* * * * *